(12) United States Patent
Donitzky et al.

(10) Patent No.: US 10,085,887 B2
(45) Date of Patent: Oct. 2, 2018

(54) TECHNIQUE FOR LASER-CUTTING AN ENDOTHELIAL CORNEAL GRAFT (71) Applicant: WAVELIGHT GMBH, Erlangen (DE)

(72) Inventors: Christof Donitzky, Eckental (DE); Theo Seiler, Zurich (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/440,591

(22) PCT Filed: Oct. 28, 2013

(86) PCT No.: PCT/EP2013/072527
§ 371 (c)(1),
(2) Date: May 4, 2015

(87) PCT Pub. No.: WO2015/062626
PCT Pub. Date: May 7, 2015

(65) Prior Publication Data
US 2016/0030243 A1 Feb. 4, 2016

(51) Int. Cl.
*A61F 9/008* (2006.01)
(52) U.S. Cl.
CPC ....... *A61F 9/00831* (2013.01); *A61F 2009/00853* (2013.01)
(58) Field of Classification Search
CPC ............... A61F 9/00831; A61F 2009/00853
USPC ..................................................... 606/2–19
See application file for complete search history.

(56) References Cited

U.S. PATENT DOCUMENTS

| 6,036,683 A * | 3/2000 | Jean .................... A61F 9/00821 606/16 |
| 7,611,507 B2 * | 11/2009 | Raksi .................... A61F 9/009 606/4 |
| 2008/0071254 A1 * | 3/2008 | Lummis ................. A61F 9/009 606/4 |
| 2011/0251601 A1 * | 10/2011 | Bissmann ........... A61F 9/00831 606/5 |

(Continued)

FOREIGN PATENT DOCUMENTS

| DE | 102008062658 A1 | 6/2010 |
| WO | 09409849 A1 | 5/1994 |

(Continued)

OTHER PUBLICATIONS

University of Iowa, Eye Donor Awarness: Frequently Asked Questions, 2016, https://www.uihealthcare.org/eye-donor-awareness-frequently-asked-questions/.*

*Primary Examiner* — Lynsey Eiseman
*Assistant Examiner* — Dacheng Xie (57) ABSTRACT

A method for preparing an endothelial corneal graft is provided. The method comprises: providing a donor cornea; irradiating the donor cornea from an endothelial side thereof with laser radiation to cause a photodisruption in tissue of the donor cornea at a focal point of the radiation; and moving the focal point of the radiation to form an endothelial graft in the donor cornea. By irradiating the donor cornea from the endothelial side thereof, instead of the epithelial side, to cut the endothelial graft, optical inhomogeneities which may develop after death in stromal tissue of the donor cornea leave the laser cutting process substantially unaffected.

13 Claims, 7 Drawing Sheets

(56) References Cited

U.S. PATENT DOCUMENTS

| | | | |
|---|---|---|---|
| 2011/0306956 A1* | 12/2011 | Islam | A61B 18/20 606/15 |
| 2014/0012295 A1* | 1/2014 | Muraine | A61F 2/142 606/166 |
| 2015/0238307 A1* | 8/2015 | Galperin | A61F 9/0081 606/41 |

FOREIGN PATENT DOCUMENTS

| | | |
|---|---|---|
| WO | 2011042031 A1 | 4/2011 |
| WO | 2012110049 A1 | 8/2012 |

* cited by examiner

TECHNIQUE FOR LASER-CUTTING AN ENDOTHELIAL CORNEAL GRAFT

CROSS REFERENCE TO RELATED APPLICATIONS

This application is a section 371 national stage phase of International Application No. PCT/EP2013/072527, filed 28 Oct. 2013, titled "TECHNIQUE FOR LASER-CUTING AN ENDOTHELIAL CORNEAL GRAFT," which is hereby incorporated by reference in its entirety.

TECHNICAL FIELD

The present disclosure generally relates to a technique for preparing an endothelial corneal graft. More specifically, and without limitation, a technique for separating at least a Descemet membrane from a donor cornea including corneal stroma is disclosed.

BACKGROUND

Aside the traditional full-thickness Penetrating Keratoplasty (PKP), eyes with permanent endothelial compromise resulting in suboptimal vision can be treated by replacing diseased parts of the cornea while retaining the healthy anterior parts of the cornea.

Posterior Lamellar Keratoplasty (PLK) was proposed by José I. Barraquer and Charles Tillett in the 1950s. The demand for precisely shaped corneal grafts increased in the late 1990s, when it was shown that a surgically resected corneal disc including diseased endothelium can be replaced with a similar partial-thickness donor disc and that the disc can be attached to the inner corneal surface of the patient's cornea without any sutures. This development led to similar surgical procedures based on differently prepared grafts.

For example, Descemet Stripping Automated Endothelial Keratoplasty (DSAEK) uses an endothelial graft, which has been prepared by mounting the donor cornea at an artificial anterior chamber and removing the anterior corneal stroma using a femtosecond laser or a microkeratome. For DSAEK, precut eye bank-prepared endothelial grafts are available, which eliminates the need for preparation of the donor corneal tissue in the operating room. However, deep anterior cuts by means of the femtosecond laser or the microkeratome can result in irregular sections, if the donor cornea is not properly mounted at the artificial anterior chamber. Furthermore, when using the femtosecond laser, the conventional preparation of the endothelial graft may be affected by optical inhomogeneities in the donor cornea, e.g., since typically more than twelve hours have passed post mortem at the time of graft preparation. E.g., the inhomogeneities can affect a focusing precision for the deep cut.

For Descemet Membrane Endothelial Keratoplasty (DMEK), the donor Descemet membrane is scored, partially detached under fluid and trephined from the endothelial side. The Descemet membrane with the healthy donor corneal endothelium is removed as a single donor disc without any donor corneal stroma. Hence, there is no need for an artificial anterior chamber or a microkeratome in the preparation of the endothelial graft. However, manually removing the Descemet membrane and the endothelium by means of mechanical trephination as well as subsequent membrane peeling for DMEK can easily cause irreparable damage to the endothelium, which does not regenerate.

SUMMARY

Accordingly, there is a need for a technique that provides an endothelial graft, which is later applicable for Descemet Stripping Endothelial Keratoplasty, from a donor cornea without impairing the Descemet membrane or the endothelium.

According to one aspect, a method of preparing an endothelial corneal graft using laser radiation comprises: providing a donor cornea isolated from a dead body; irradiating the donor cornea from an endothelial side thereof with laser radiation to cause a photodisruption in tissue of the donor cornea at a focal point of the radiation; and moving the focal point of the radiation to form an endothelial graft in the donor cornea.

The donor cornea may be provided from a dead human body. Alternatively, the donor cornea may be provided isolated from a living body, e.g., from a living human body.

Providing the donor cornea may include deforming the donor cornea to have a curvature opposite to a natural curvature of the donor cornea. Providing the donor cornea may include placing an endothelium of the donor cornea in contact with a reference contact surface of a laser apparatus generating the laser radiation.

The method may comprise: determining a thickness of a predetermined structure of the donor cornea, the predetermined structure formed by one of an endothelium, a Descemet membrane and a Dua layer of the donor cornea or a combination thereof; and based on the determined thickness of the predetermined structure, determining a desired thickness of the endothelial graft; wherein moving the focal point of the radiation includes moving the focal point across a surface that is a distance corresponding to the desired thickness of the endothelial graft from the reference contact surface. The desired thickness of the endothelial graft may be determined to be in a range from 30 to 120 µm, e.g., 90 µm. The surface may extend at least substantially parallel to the reference contact surface.

The term Descemet membrane, as used herein, may also encompass the Dua layer. The Descemet membrane and the Dua layer may be considered as two manifestations of one common structure, which may be commonly referred to as the Descemet membrane. E.g., the Dua layer may be considered as a crossover from the stroma to the Descemet membrane.

Providing the donor cornea may include positioning the donor cornea on a support unit in opposition to a reference contact surface of a laser apparatus generating the laser radiation.

Irradiating the donor cornea may include focusing the laser radiation in stromal tissue of the donor cornea, wherein moving the focal point of the radiation includes moving the focal point through the stromal tissue to create a stromal bed cut for the graft. At least a major part of the bed cut may extend substantially parallel to a Descemet membrane of the donor cornea. A desired distance between the bed cut and a Descemet membrane may be selected in the range from 5 µm to 100 µm, e.g., 50 µm, and the focal point of the radiation is moved through the stromal tissue at the selected distance from the Descemet membrane. The desired distance may be selected differently for different wavelengths of the radiation.

The focal point of the radiation may be moved so as to leave undisrupted a connection structure connecting the endothelial graft with surrounding tissue of the donor cornea. The connection structure may be formed entirely by stromal tissue of the donor cornea.

According to another aspect, a method of configuring a control unit of an ophthalmic laser apparatus is provided. The control unit is adapted to control movement of a focal point of a laser beam relative to a reference contact surface of the laser apparatus, the reference contact surface having a known position in a coordinate system of the laser apparatus. The method comprises: determining a thickness of a predetermined structure of a donor cornea isolated from a dead body, the predetermined structure being formed by one of an endothelium, a Descemet membrane and a Dua layer of the donor cornea or a combination thereof; based on the determined thickness of the predetermined structure, determining a desired thickness of an endothelial graft to be prepared from the donor cornea; and configuring the control unit to move the focal point across a surface that is a distance corresponding to the desired thickness of the endothelial graft from the reference contact surface of the laser apparatus. When the predetermined structure is formed by the Descemet membrane, the predetermined structure may also comprise a structure that is referred to as Dua layer in literature.

The donor cornea may be provided from a dead human body. Alternatively, the donor cornea may be provided isolated from a living body, e.g., from a living human body.

Yet another aspect provides the use of an ophthalmic laser apparatus for preparing an endothelial graft in a donor cornea isolated from a dead body, the apparatus comprising: a source of laser radiation; a reference contact surface having a known position in a coordinate system of the laser apparatus, the reference contact surface being transmissive for the laser radiation; and a control unit configured to control movement of the focal point of the laser radiation relative to the reference contact surface; wherein the use comprises: mounting the donor cornea on a support unit with an endothelium of the donor cornea contacting the reference contact surface; irradiating the donor cornea with the laser radiation through the reference contact surface; and causing the control unit to move the focal point of the laser radiation through the donor cornea to create the endothelial graft. In the use, the control unit may be cause to move the focal point of the laser radiation across a surface that is no more than 90 μm or 80 μm or 70 μm or 60 μm or 50 μm or 40 μm or 30 μm from the reference contact surface to thereby create a stromal bed cut for the endothelial graft.

The donor cornea may be provided from a dead human body. Alternatively, the donor cornea may be provided isolated from a living body, e.g., from a living human body.

According to still another aspect, a method of preparing an endothelial graft from a donor cornea isolated from a dead body is provided, the endothelial graft including a Descemet membrane, the donor cornea including stromal tissue. The method comprises the steps of providing a support unit for supporting the donor cornea; providing a cutting laser apparatus including a cutting laser interface configured for directing radiation towards the support unit; mounting the donor cornea at the support unit so that at least the Descemet membrane is arranged between the corneal stroma and the cutting laser interface; and controlling a focus of the radiation according to a control program including instructions that cause the radiation to pass through the Descemet membrane and to focus within the corneal stroma at focal points defining a bed cut within the corneal stroma that is at least substantially parallel to the Descemet membrane.

The donor cornea may be provided from a dead human body. Alternatively, the donor cornea may be provided isolated from a living body, e.g., from a living human body.

The donor cornea may be a heterograft, e.g., a human donor cornea, or a xenograft. The cornea may be removed from a dead body. The graft and the donor cornea may include any one or any combination of a corneal endothelium, the Descemet membrane and a Dua layer. Herein, the Descemet membrane may be considered as a layer distinct from the Dua layer or as a structure that also comprises the Dua layer. The graft can be subjected to cryogenic storage and/or later be used for endothelial keratoplasty, e.g., in cases of Fuchs dystrophy, bullous keratopathy, iridocorneal endothelial (ICE) syndrome, or other endothelial disorder.

A conventional cutting laser apparatus and/or a conventional support unit may be used. The donor cornea may be inversely mounted at the support unit, i.e. with the endothelium of the donor cornea facing toward the cutting laser interface and the epithelium of the donor cornea facing away from the cutting laser interface. The cutting laser interface may provide a reference contact surface for an object to be laser-treated by means of the laser apparatus. Upstream of the focal point, the radiation may pass through at least one of the Dua layer, the Descemet membrane and the corneal endothelium of the donor cornea. The radiation may cross the Descemet membrane once. The inverse orientation of the donor cornea relative to the cutting laser interface can, for at least certain donor corneas, improve the precision, e.g., a shape and/or a position, of a focal point for performing the laser cut, reduce attenuation of the radiation and/or reduce scattering of the radiation, e.g., compared to a conventional preparation suffering from attenuation and/or scattering due to inhomogeneities in the corneal stroma.

The radiation may be focused at a sequence of points in a cutting plane (surface) for the bed cut. Subsequent points of the sequence may be spaced apart to allow dissipation of locally introduced heat.

The bed cut may be spaced apart from the Descemet membrane by any value in the range from 5 μm to 50 μm. The distance between the Descemet membrane and the bed cut may be selected depending on a wavelength of the radiation. The distance may be selected to be anywhere in the range from 10 μm to 50 μm for infrared radiation. The distance may be selected to be anywhere in the range from 5 μm to 20 μm for ultraviolet radiation. Herein, the Descemet membrane may be considered as a layer distinct from the Dua layer or as a structure that also comprises the Dua layer.

An energy density of the radiation may be below a cutting threshold in any one of the Dua layer, the Descemet membrane (optionally including a structure that is also referred to as Dua layer) and the corneal endothelium. The energy density of the radiation may exceed the cutting threshold inside the corneal stroma.

The mounting may include inverting a natural curvature of the donor cornea. The natural shape of a human cornea may be that of a bowl, with the epithelium on the outer side of the bowl and the endothelium on the inner side. The natural curvature may be inverted due to a shape of the support unit and/or manually or by other means prior to mounting the donor cornea at the support unit. The mounting may include clamping a marginal area of the donor cornea.

The cutting laser interface may include a transparent contact surface facing towards the support unit. The contact surface may be planar or concave. The bed cut may extend at least substantially parallel to the contact surface. A distance between the contact surface of the cutting laser interface and the focal points defining the bed cut may be in the range of 20 μm to 100 μm, preferably 30 μm to 90 μm.

The cutting laser interface and the support unit may be arranged on an optical axis. The optical axis may intersect the Descemet membrane substantially perpendicularly. The bed cut may extend parallel to at least one of the Dua layer, the Descemet membrane and the corneal endothelium.

The instructions may further control a circumferential cut through the donor cornea. The circumferential cut may be at least substantially perpendicular to the contact surface. The circumferential cut may range from one side of the corneal graft facing the contact surface to at least the bed cut, e.g., to the other side of the corneal graft facing the support unit.

The bed and circumferential cuts may separate the graft from at least a part of the corneal stroma. Alternatively, the bed and circumferential cuts may substantially separate the graft from the corneal stroma except for a tearable connection with the corneal stroma. The tearable connection may include one, two or three laterally separated connections. Each of the laterally separated connections may have a cross section of 100 μm×100 μm or less, or may have any other geometrical shape (e.g., an ellipse or circle) of corresponding size. Alternatively or in combination, the corneal stroma may remain connected with the graft along a circumferential line, preferably a circle. The circumferential line may be closed or perforated. A thickness of the circumferential line, e.g., in a radial direction, may be less than 50 μm, preferably less than 20 μm.

The support unit may include a fluid-filled chamber supporting the corneal stroma. The fluid-filled chamber may be an artificial anterior chamber. The chamber may include a recess, e.g., in an at least partially planar surface of the support unit facing towards the cutting laser interface. The recess may be covered by the mounted donor cornea. E.g., the recess and the mounted donor cornea may enclose the chamber. The chamber may be formed by the recess and the mounted donor cornea. A boundary region of the donor cornea may circumferentially abut against the surface, e.g., so as to seal the chamber.

The recess may include one or more openings for injecting air, a balanced salt solution and/or a viscoelastic. The chamber may be pressurized using a fluid, e.g., air. The pressurized donor cornea may abut against the contact surface. The pressure may define a contact pressure of the graft abutting against the contact surface.

A method of generating a control program for preparing an endothelial graft including a Descemet membrane from a donor cornea, e.g., isolated form a dead body, and having stromal tissue is also provided. The method comprises the steps of determining a thickness of any one or any combination of a corneal endothelium, the Descemet membrane and a Dua layer of the donor cornea; and generating a control program for a control unit configured for controlling a focus of radiation according to the control program, the control program including instructions that depend on the determined thickness and, when executed by the control unit, cause the radiation to pass through the Descemet membrane and to focus within the corneal stroma at focal points defining a bed cut within the corneal stroma that is at least substantially parallel to the Descemet membrane.

The donor cornea may be provided from a dead human body. Alternatively, the donor cornea may be provided isolated from a living body, e.g., from a living human body.

Herein, the Descemet membrane may be considered as a layer distinct from the Dua layer or as a structure that also comprises the Dua layer.

The thickness may be determined, e.g., by means of Optical Coherence Tomography (OCT) and/or by means Optical Low Coherence Reflectometry (OLCR).

According to yet another aspect, a computer program product is provided. The computer program comprises program code for carrying out one or more of the method steps disclosed herein, when the computer program product is executed on one or more computing devices. Moreover, a computer readable recording medium is provided that stores the computer program product. The computer program product may also be provided for download to such a recording medium, e.g., via the Internet.

BRIEF DESCRIPTION OF THE DRAWINGS

In the following, the invention will be described in more detail with reference to exemplary embodiments illustrated in the drawings, wherein FIG. 1 schematically illustrates a laser system for preparing an endothelial corneal graft.

DETAILED DESCRIPTION

Figure 1:
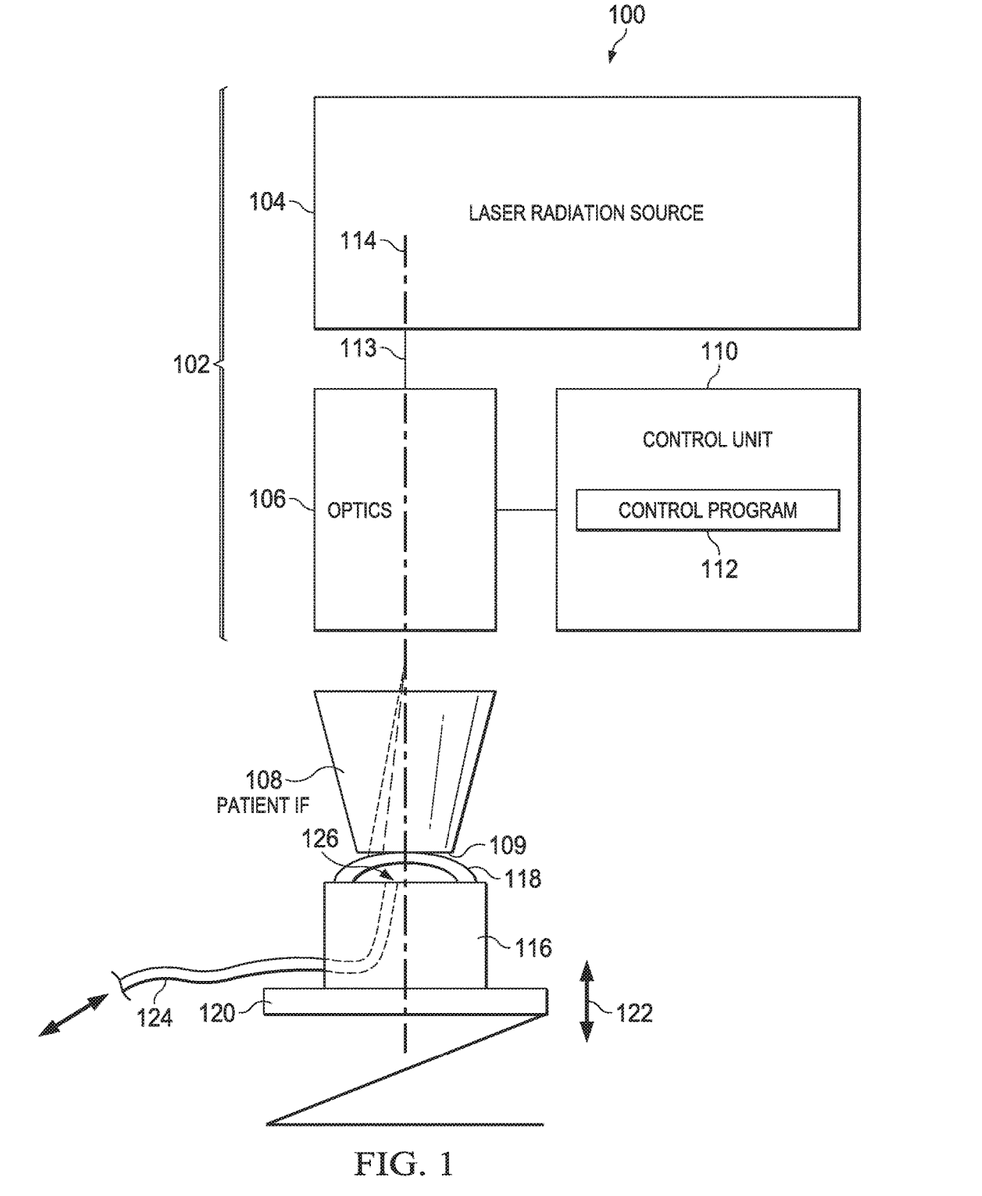

FIG. 1 schematically illustrates a laser system 100 equipped to allow a surgeon to prepare an endothelial graft from a donor cornea removed from a dead body. The laser system 100 comprises a cutting laser apparatus 102 and a support unit 116. The cutting laser apparatus 102 includes a source 104 of laser radiation, focusing and deflecting optics 106, and a cutting laser interface 108 (sometimes referred to as a patient interface, or adapter, when the cutting laser apparatus 102 is used for laser-treatment). The cutting laser apparatus 102 further comprises a control unit 110 including a control program 112.

The source 104 generates pulsed laser radiation 113 propagating along an optical axis 114. The pulse duration of the laser pulses is in the alto-, femto-, pico- or nanosecond range. The energy density (i.e. fluence) and intensity of the pulses is suitably selected to achieve a photodisruption (which includes a laser-induced optical breakdown) in human corneal tissue as a result of the irradiation of a particular tissue location with a pre-defined number of pulses (one or more). The focusing and deflecting optics 106 includes a scanning device (including e.g., one or more galvanometer mirrors or adaptive mirrors) for laterally deflecting the radiation 113, i.e. in a direction transverse to the optical axis 114. The focusing and deflecting optics 106 is further configured to focus the radiation at positions closely below the cutting laser interface 108. The focusing and deflecting optics 106 may be electrically connected, e.g., by wire or wirelessly, to the control unit 110, which controls the focus position and the deflection of the radiation 113 according to instructions of the control program 112.

The radiation 113 is directed through the cutting laser interface 108 towards the support unit 116, which is configured for inversely supporting a donor cornea 118. The support unit 116 is arranged on a basis 120, which is height-adjustable (as represented by a double-arrow 122). A line 124 provides a fluid connection into an artificial anterior chamber 126. The chamber 126 supports the inversely mounted donor cornea so that an endothelium of the donor cornea 118 faces the cutting laser interface 108.

Figure 2:
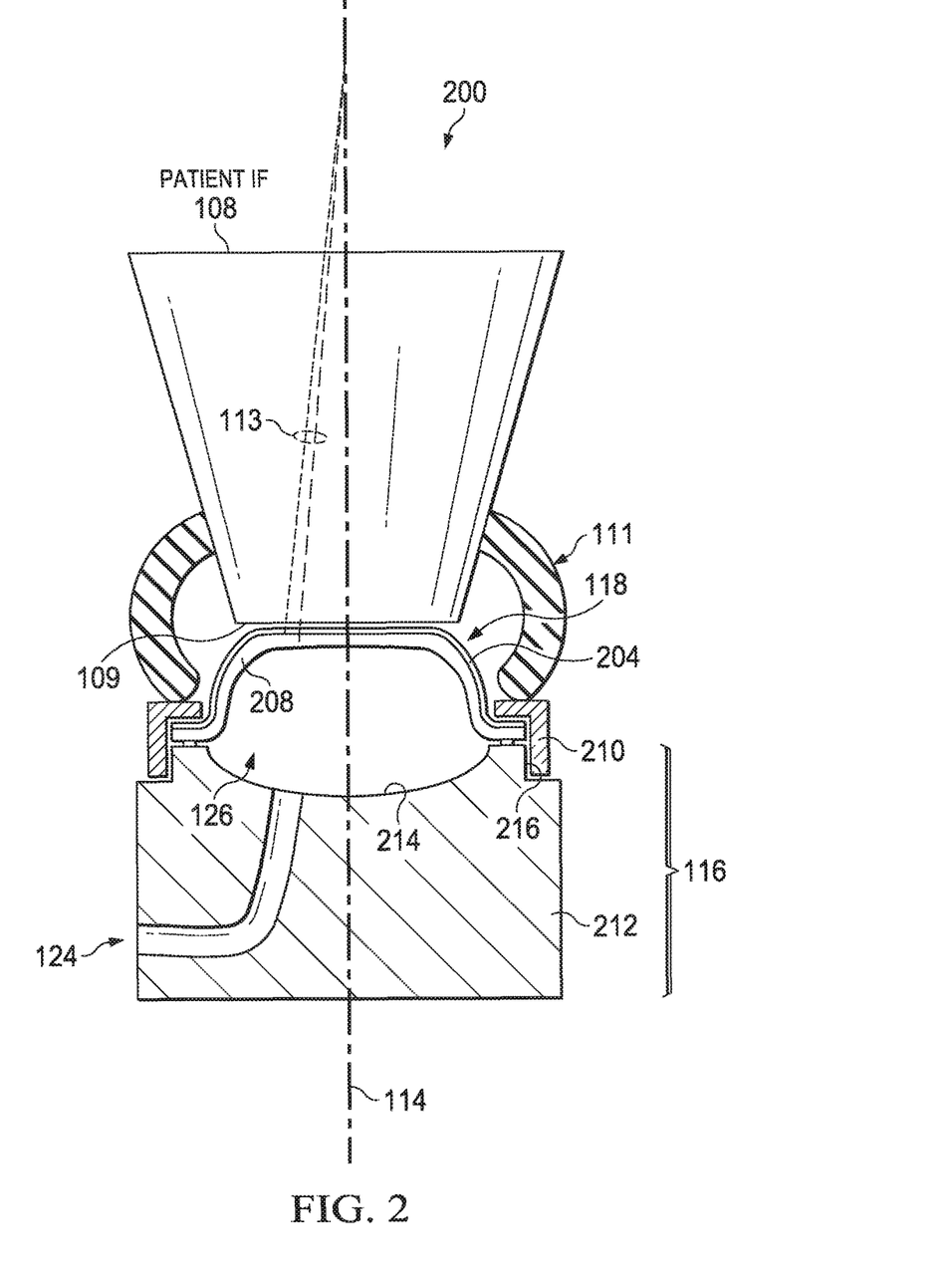
FIG. 2 shows a schematic cross-sectional view including details of the laser system of FIG. 1.

FIG. 2 schematically illustrates a cross-sectional view 200 of the cutting laser interface 108, the mounted donor cornea 118 and the support unit 116 in a section including the optical axis 114.

The donor cornea 118 is inversely arranged at the support unit 116. The pressure in the chamber 126 causes the donor cornea 118 to planarly abut with its posterior side (i.e. endothelial side) against a reference contact surface 109 of the cutting laser interface 108. The reference contact surface 109 may be formed, in a manner generally known per se, from a contact member (e.g., applanation plate, contact lens) which is transparent to the laser radiation 113. Optionally, an enclosure 111 circumferentially encloses the contact surface 109. One end of the enclosure 111 is mounted at a conical surface of the cutting laser interface 108. Another end of the enclosure 111 is resilient and contacts a flat upper surface of the support unit 116. A vacuum is applied to the volume enclosed by the enclosure 111 to further facilitate the planar contact between the donor cornea 118 and the contact surface 109.

The support unit 116 includes a clamping ring 210 and a socket 212. The socket 212 includes a recess 214 in an upper surface of the socket 212, e.g., a surface of the socket 212 closest to the contact surface 109. The line 124 fluidly connects an inlet opening at or outside the socket 212 with an opening in the recess 214. The inlet opening is external to the chamber 126. The opening in the recess is inside the chamber 126. A circumferential edge 216 in the upper surface of the socket 212 is configured for receiving the clamping ring 210. The donor cornea 118 is mounted at the support unit 116 by clamping a boundary area of the donor cornea 118 between the clamping ring 210 and the socket 212.

The donor cornea includes at least a Descemet membrane 204 and corneal stroma 208. The endothelial graft to be prepared includes at least the Descemet membrane 204.

Figure 3:
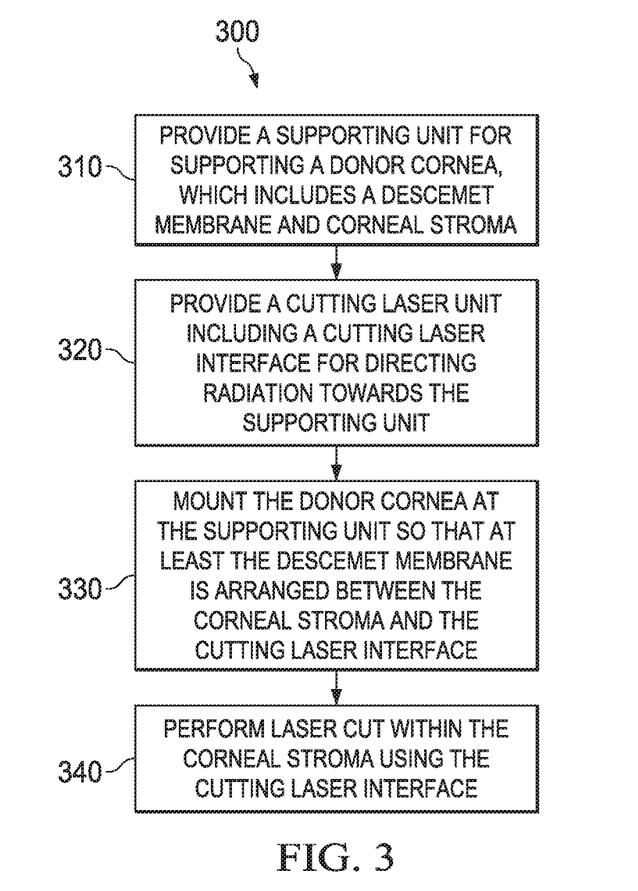
FIG. 3 shows a flowchart for a method embodiment that can be performed by the laser system of FIG. 1.

FIG. 3 shows a flowchart of a method 300 for preparing an endothelial graft including at least a Descemet membrane from a donor cornea that further includes at least corneal stroma. In a step 310 of the method 300, a support unit is provided for supporting a donor cornea that includes the Descemet membrane and the corneal stroma. In a step 320, a cutting laser apparatus is further provided including a cutting laser interface for directing radiation towards the support unit. The donor cornea is mounted at the support unit in a step 330. The donor cornea is inversely mounted, i.e., in an orientation so that at least the Descemet membrane is arranged between the corneal stroma and the cutting laser interface. In a step 340, a laser cut within the corneal stroma is performed using the cutting laser interface 108.

Figure 4A:
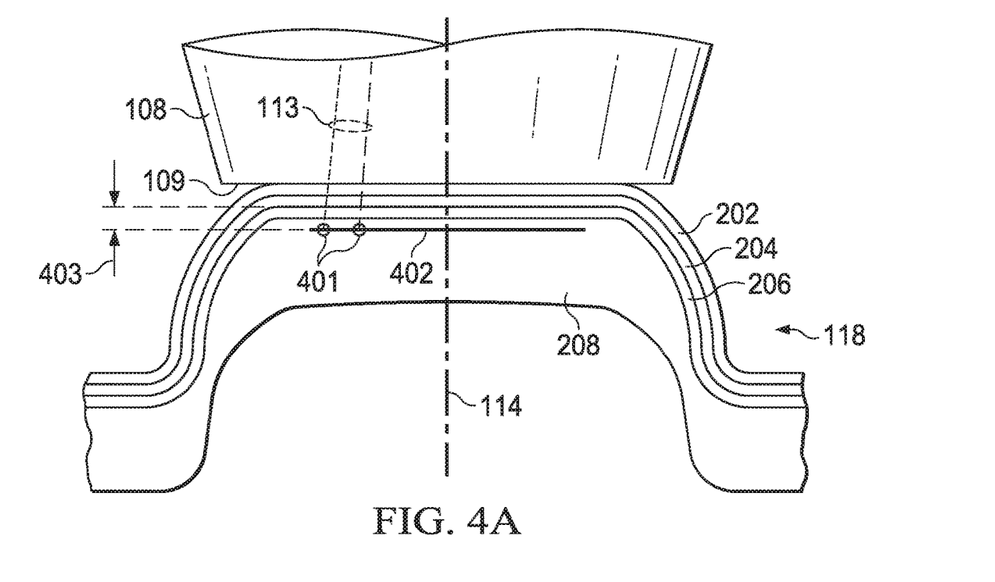
FIGS. 4A, 4B, and 4C schematically illustrate focal point sets for performing a bed cut and a circumferential cut in the donor graft.

FIG. 4A schematically illustrates a cross-sectional view of the laser cut performed according to the step 340 by the radiation 113 transmitted through the cutting laser interface 108. The viewing plane of FIG. 4A includes the optical axis 114. The step 340 is controlled by the control unit 110. The donor cornea 118 includes an endothelium 202, the Descemet membrane 204, a Dua layer 206 and the corneal stroma 208. The endothelium 202 abuts against the contact surface 109 of the cutting laser interface 108.

The radiation 113 is focused at a sequence of exemplary focal points 401 within the corneal stroma 208. The sequence of focal points defines a bed cut 402 that is, at least substantially, perpendicular to the optical axis 114 and completely inside the corneal stroma 208 of the donor cornea 118.

The bed cut 402 is spaced apart from the Descemet membrane 204 (or the Dua layer 206) by a safety distance 403. The safety distance 403 prevents damage caused by cavitation shockwaves due to cavitation bubbles created by the radiation 113 at the focal points 401. The safety distance 403 depends on the fluence, i.e. pulse energy used for the radiation 113. The technique disclosed herein can be realized using, e.g., an infrared (IR) femtosecond laser or an ultraviolet (UV) femtosecond laser. For IR radiation 113, the safety distance 403 is larger than the safety distance used for UV radiation 113. For example, the safety distance 403 is in the range of 10 µm to 50 µm for IR radiation 113. For UV radiation, the safety distance 403 is in the range of 5 µm to 20 µm.

Figure 4B:
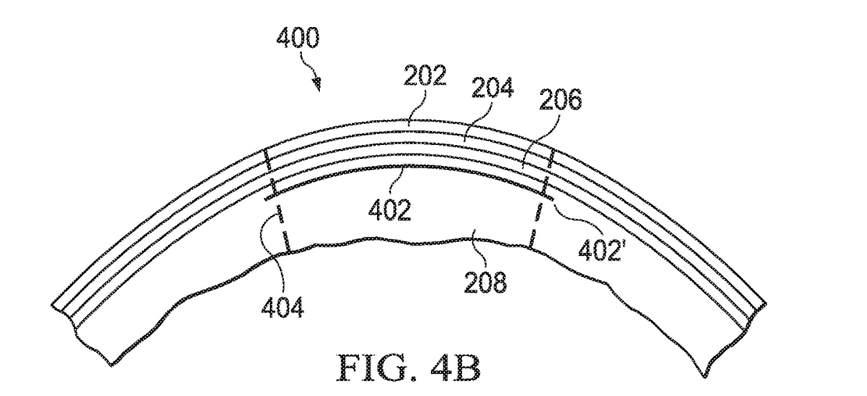

FIG. 4B schematically illustrates a cross-section of a graft 400 as a result of the method 300. The cross-sectional view in FIG. 4B shows the graft 400 in the everted configuration used for the step 340.

The method 300 may further include performing a circumferential cut 404 from a backside of the donor cornea 118 to a frontside of the donor cornea 118. The circumferential cut 404 is indicated by a dashed line in FIGS. 4B and 4C. The circumferential cut 404 is preferably rotationally symmetric with respect to the optical axis 114. The boundary defined by the circumferential cut 404 may include straight lines and/or kinks. E.g., the circumferential cut 404 can be performed and shaped as described in document WO 2012 076033 A1. The circumferential cut 404 is also referred to as side cuts. In one implementation of the method 300, a conical circumferential cut 404 is performed. The conical cut 404 may, in a cross-section including the optical axis 114, include a predefined angle with the optical axis 114. The angle may be in a range of 5° to 40° with respect to the optical axis 114. In another implementation of the method 300, the circumferential cut 404 has Z-shaped line segments in a cross-section including the optical axis 114. Corresponding Z-shaped lines may be provided in an eye receiving the graft for a positive fit and improved healing.

Figure 4C:
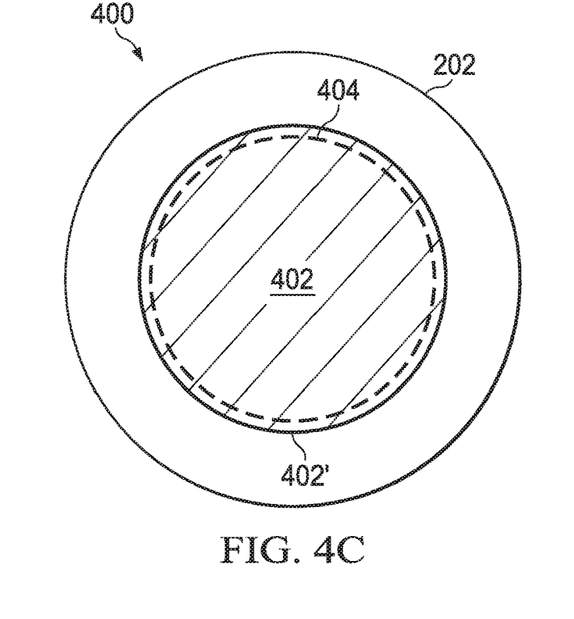

FIG. 4C schematically illustrates the graft 400 in a viewing plane perpendicular to the optical axis 114. A hatched area represents the cut 402 within its circular border line 402', which is also indicated in the cross-sectional view of FIG. 4B.

In one embodiment of the apparatus 100 and the method 300, the circumferential cut 404 is performed by means of the cutting laser apparatus 102 according to further instructions included in the control program 112. Alternatively, the circumferential cut 404 is performed by means of a cornea button punch or a radial vacuum trephine.

Figure 5A:
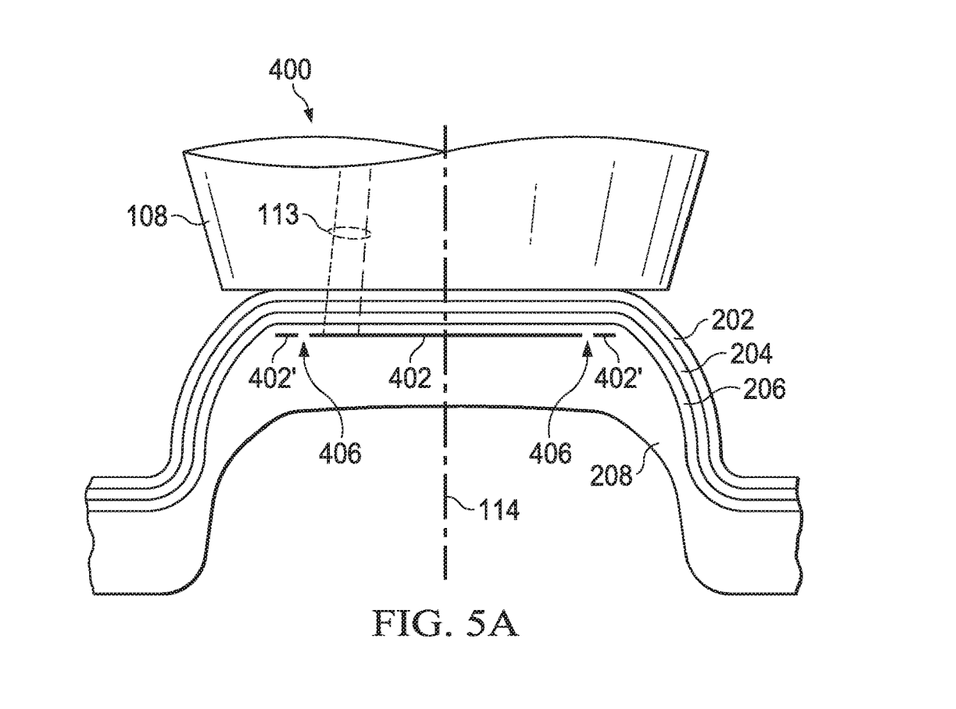
FIGS. 5A, 5B, 5C and 5D schematically illustrate variants of the focal point sets for preparing one or more stromal connections.
Figure 5B:
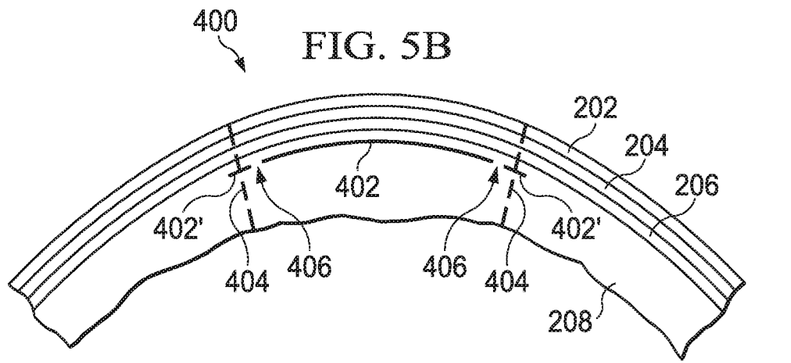
Figure 5C:
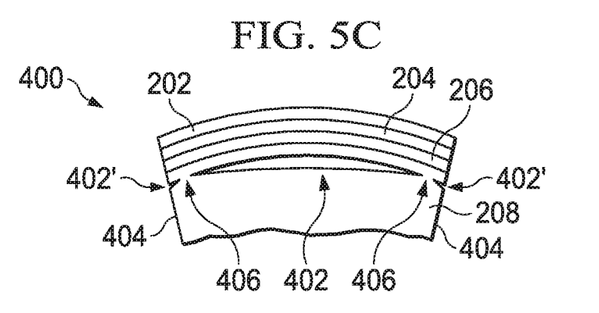

FIG. 5A shows a cross-sectional view of a variant of the bed cut 402 performed in the step 340. The bed cut 402 is performed similar to the bed cut 402 described with reference to FIG. 4A except for one or more connections 406 that remain uncut for connecting the endothelial graft 400 and the stroma 208. When the circumferential cut 404 crosses the bed cut 402 between the connection 406 and the border line 402' of the bed cut 402, as shown in FIG. 5B, the resulting graft 400 remains connected via a minimal bridge connection 406 close to or at the boundary of the graft 400, as is shown in FIG. 5C.

Figure 5D:
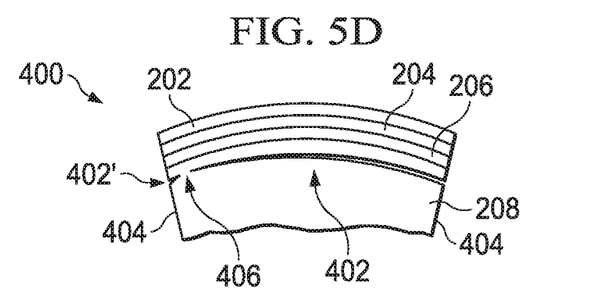

FIG. 5D schematically illustrates a cross-sectional view of a further variant of the bed cut 402 for a minimal point connection 406. The point connection 406 can be arranged close to or at the boundary of the graft 400.

While the exemplary bed cuts 402 shown in FIG. 5A to 5D include a boundary cut 402', the connection 406 alternatively coincides with the boundary 404 of the graft 400. For example, the circumferential cut 404 defining the boundary of the graft 400 passes through the connection 406 without crossing the bed cut 402. For the benefit of a precise relative arrangement of the bed cut 402 and the circumferential cut 404, the circumferential cut 404 is also performed by the cutting laser apparatus 102 performing the bed cut 402, e.g., while the donor cornea 118 stays inversely mounted at the support unit 116.

Figure 6:
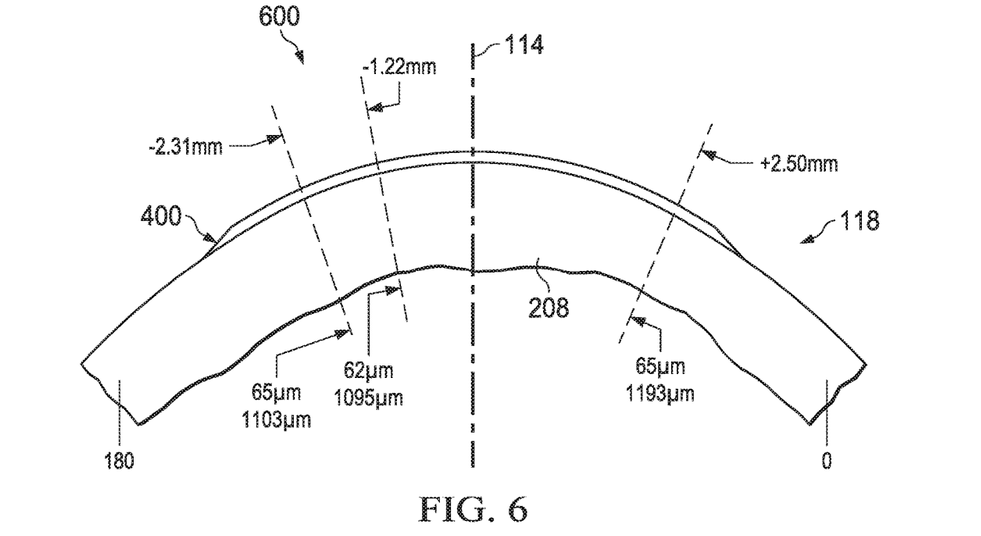
FIGS. 6 and 7 show cross-sectional views of examples of a donor cornea in an inverted orientation after creation of a bed cut.
Figure 7:
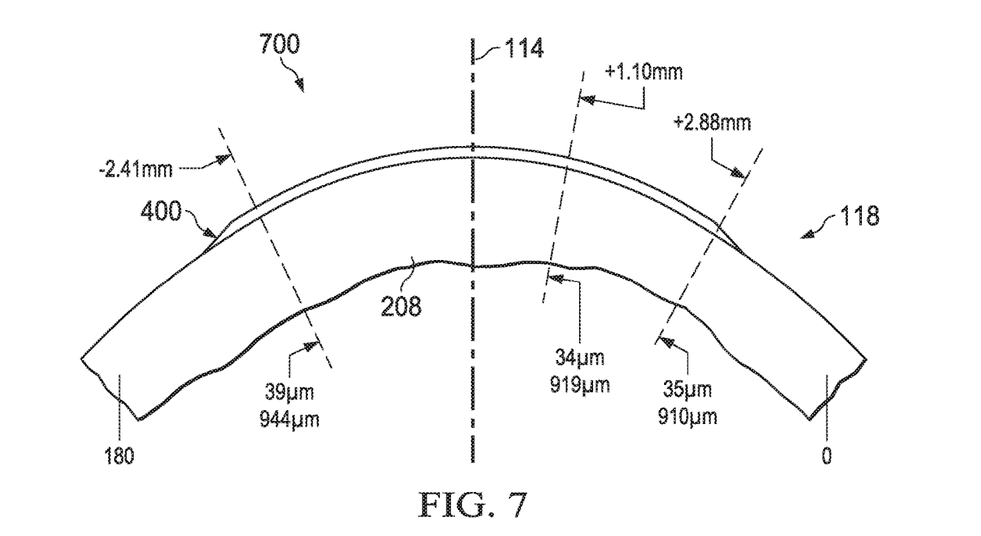

The endothelial graft 400 is a thin lamella, e.g., 30 μm to 90 μm in thickness. FIGS. 6 and 7 show cross-sectional views of the donor cornea 118 after performing the bed cut 402 according to the step 340. The viewing plane in FIGS. 6 and 7 includes the optical axis 114. In the Optical Coherence Tomography (OCT) images 600 and 700, the endothelial graft 400 is visible as a curved white line at the upper surface of the cut donor cornea 118. The curved white line indicating the endothelial graft 400 at the endothelial side of the donor cornea 118 includes the endothelium 202 and the Descemet membrane 204.

The OCT image 600 shows the graft 400 separated from the donor cornea 118 along the bed cut 402 performed using IR radiation 113. The graft 400 shown in the OCT image 700 is prepared using UV radiation 113.

The inverted curvature configuration of the cut donor cornea 118 shown in the OCT images 600 and 700 can be seen from the formation of folds at the anterior side (shown as the bottom surface in the OCT images 600 and 700) of the corneal stroma 208.

Distance values shown in FIGS. 6 and 7 above the upper surface of the graft 400, i.e., near the endothelial side of the graft 400, indicate an arc length from the optical axis 114. Negative values are used on the left-hand side and positive distance values on the right-hand side relative to the optical axis 114.

Below the bottom surface of the donor cornea 118, pairs of thickness values are shown. The upper smaller value indicates the thickness of the endothelial graft 400 measured at the lateral position indicated by the corresponding straight line. The greater value (shown below the graft thickness value) indicates the thickness of the corneal stroma 208 included in the donor cornea 118 and separated from the endothelial graft by the bed cut 402. For the exemplary cut 402 shown in the OCT image 600, a graft thickness of 65 μm and a stroma thickness of 1103 μm have been observed at the lateral position −2.31 mm, a graft thickness of 62 μm and a stroma thickness of 1095 μm have been observed at the lateral position −1.22 mm, and a graft thickness of 65 μm and a stroma thickness of 1193 μm have been observed at the lateral distance +2.50 mm. The separation between stroma 208 and endothelial graft 400 is visible at the lateral position +2.50 mm as a black stripe in the OCT image 600.

For the exemplary cut 402 shown in the OCT image 700, a graft thickness of 39 μm and a stroma thickness of 944 μm have been observed at the lateral position −2.41 mm, a graft thickness of 34 μm and a stroma thickness of 919 μm have been observed at the lateral position +1.10 mm, and a graft thickness of 35 μm and a stroma thickness of 910 μm have been observed at the lateral position +2.88 mm. The separation due to the bed cut 402 is visible as a black stripe in the OCT image 700 at the lateral positions −2.41 mm and +1.10 mm.

As has become apparent based on above exemplary embodiments of the method 300 performed by the apparatus 100, an endothelial graft can be prepared by a precise bed cut independently of optical inhomogeneities in the corneal stroma. One or more small connection structures (e.g., connection bridges) at or near the boundary of the graft to the stroma can ensure that the prepared endothelial graft does not accidentally separate from the support unit. Furthermore, one or more connections structures can indicate the orientation of the endothelial graft. E.g., after the preparation of the graft, the connected stroma can indicate simply by visual inspection that the opposite side includes the endothelium of the graft, which is otherwise not visible.

The technique can also prepare an endothelial graft that is later applicable for Posterior Lamellar Keratoplasty, including Deep Lamellar Endothelial Keratoplasty (DLEK). E.g., the instructions in the control program may specify a thickness of the endothelial graft, so that a corneal stroma layer thicker than the safety distance is included in the endothelial graft.

The invention claimed is:

1. A method of preparing an endothelial corneal graft using laser radiation, the method comprising:
    providing a donor cornea isolated from a dead body by inverting a natural curvature of the donor cornea, wherein a natural shape is that of a bowl with an epithelium layer on an outer side of the bowl and an endothelium layer on the inner side, and an inverted shape has the epithelium layer on the inner side and the endothelium layer on the outer side;
    clamping the donor cornea with an inverted shape onto a socket, forming an artificial interior chamber between the endothelium layer and the socket, the socket further including a fluid line;
    arranging the socket such that the donor cornea is positioned between the socket and a contact surface contact surface of a cutting laser interface of a laser apparatus that generates the laser radiation;
    pressuring, using the fluid line, the artificial interior chamber to cause the endothelium layer to abut the contact surface of the cutting laser interface;
    irradiating the donor cornea from the endothelial side thereof with laser radiation to cause a photodisruption in tissue of the donor cornea at a focal point of the radiation; and
    moving the focal point of the radiation to form an endothelial graft in the donor cornea.

2. The method of claim 1, comprising:
    determining a thickness of a predetermined structure of the donor cornea, the predetermined structure formed by one of an endothelium, a Descemet membrane and a Dua layer of the donor cornea or a combination thereof;
    based on the determined thickness of the predetermined structure, determining a desired thickness of the endothelial graft;
    wherein moving the focal point of the radiation includes moving the focal point across a surface that is a distance corresponding to the desired thickness of the endothelial graft from the reference contact surface.

3. The method of claim 2, wherein the desired thickness of the endothelial graft is determined to be in a range from 30 to 120 μm.

4. The method of claim 2, wherein the surface extends at least substantially parallel to the reference contact surface.

5. The method of claim 1, wherein providing the donor cornea includes positioning the donor cornea on a support unit in opposition to the contact surface of a laser apparatus generating the laser radiation.

6. The method of claim 1, wherein irradiating the donor cornea includes focusing the laser radiation in stromal tissue of the donor cornea, wherein moving the focal point of the radiation includes moving the focal point through the stromal tissue to create a stromal bed cut for the graft.

7. The method of claim 6, wherein at least a major part of the bed cut extends substantially parallel to a Descemet membrane of the donor cornea.

8. The method of claim 6, comprising: selecting a desired distance between the bed cut and a Descemet membrane in the range from 5 μm to 100 μm, wherein moving the focal point of the radiation includes moving the focal point through the stromal tissue at the selected distance from the Descemet membrane.

9. The method of claim 8, wherein selecting a desired distance includes selecting the desired distance differently for different wavelengths of the radiation.

10. The method of claim 1, wherein moving the focal point of the radiation includes moving the focal point so as to leave undisrupted a connection structure connecting the endothelial graft with surrounding tissue of the donor cornea.

11. The method of claim 10, wherein the connection structure is formed by stromal tissue of the donor cornea.

12. The method of claim 5, further comprising:
enclosing the donor cornea in a volume between the support unit and the contact surface of the laser apparatus.

13. The method of claim 12, further comprising:
creating a vacuum in the enclosed volume between the support unit and the contact surface of the laser apparatus to further abut the endothelium and a contact surface of a laser apparatus.

* * * * *

UNITED STATES PATENT AND TRADEMARK OFFICE
CERTIFICATE OF CORRECTION

PATENT NO. : 10,085,887 B2
APPLICATION NO. : 14/440591
DATED : October 2, 2018
INVENTOR(S) : Christof Donitzky et al.

Page 1 of 1

It is certified that error appears in the above-identified patent and that said Letters Patent is hereby corrected as shown below:

On the Title Page

(71) Applicant reads: WAVELIGHT GMBH, Erlangen (DE)
Should read: NOVARTIS AG, Basel (CH)

Signed and Sealed this
Fifth Day of March, 2019

Andrei Iancu
*Director of the United States Patent and Trademark Office*